United States Patent [19]
Beal

[11] Patent Number: 5,849,782
[45] Date of Patent: Dec. 15, 1998

[54] METHODS OF INHIBITING NEURODEGENERATIVE DISEASES

[75] Inventor: M. Flint Beal, Boston, Mass.

[73] Assignee: The General Hospital Corporation, Boston, Mass.

[21] Appl. No.: 679,313

[22] Filed: Jul. 12, 1996

Related U.S. Application Data

[63] Continuation of Ser. No. 373,302, Jan. 13, 1995, abandoned.

[51] Int. Cl.$^6$ .......................... A61K 31/21; A61K 31/255
[52] U.S. Cl. ............................................. 514/418; 514/415
[58] Field of Search ...................................... 514/418, 415

[56] References Cited

U.S. PATENT DOCUMENTS 5,266,594  11/1993  Dawson et al. .......................... 514/560

FOREIGN PATENT DOCUMENTS

| | | |
|---|---|---|
| 0 446 699 A1 | 9/1991 | European Pat. Off. . |
| 0 547 558 A1 | 6/1993 | European Pat. Off. . |
| 0 558 468 A1 | 9/1993 | European Pat. Off. . |
| WO 93/13055 | 7/1993 | WIPO . |
| WO 93/13066 | 7/1993 | WIPO . |
| WO 94/12163 | 6/1994 | WIPO . |
| WO 94/12165 | 6/1994 | WIPO . |
| WO 94/21621 | 9/1994 | WIPO . |
| WO 85/05363 | 2/1995 | WIPO . |
| WO 95/10266 | 4/1995 | WIPO . |
| WO 95/11014 | 4/1995 | WIPO . |
| WO 95/11231 | 4/1995 | WIPO . |
| PCT/US96/00446 | 4/1996 | WIPO . |

OTHER PUBLICATIONS

Moore, P.K. et al., British Journal of Pharmacology, vol. 108, No. 2, issued Feb. 1993, pp. 296–297.

Babbage et al; "Indazoles a novel group of Nitric Oxide Synthase Inhibitors", 1993 British J. of Pharm. vol. 109 Sup. 142p Merck Manual of Diagnosis & Therapy; Sixteenth Edition, Division of Merck & Co Inc pp. 1512–1513 (1992).

*Primary Examiner*—Theodore J. Criares
*Attorney, Agent, or Firm*—Fish & Richardson P.C.

[57] ABSTRACT

Methods for inhibiting a nitric oxide-mediated pathological condition and a neurodegenerative disease such as Parkinson's disease, Huntington's disease, Alzheimers's disease, and amyotrophic lateral sclerosis in a human patient, comprising administering an effective amount of a nitroindazole capable of inhibiting a neuronal nitric oxide synthase.

7 Claims, 13 Drawing Sheets

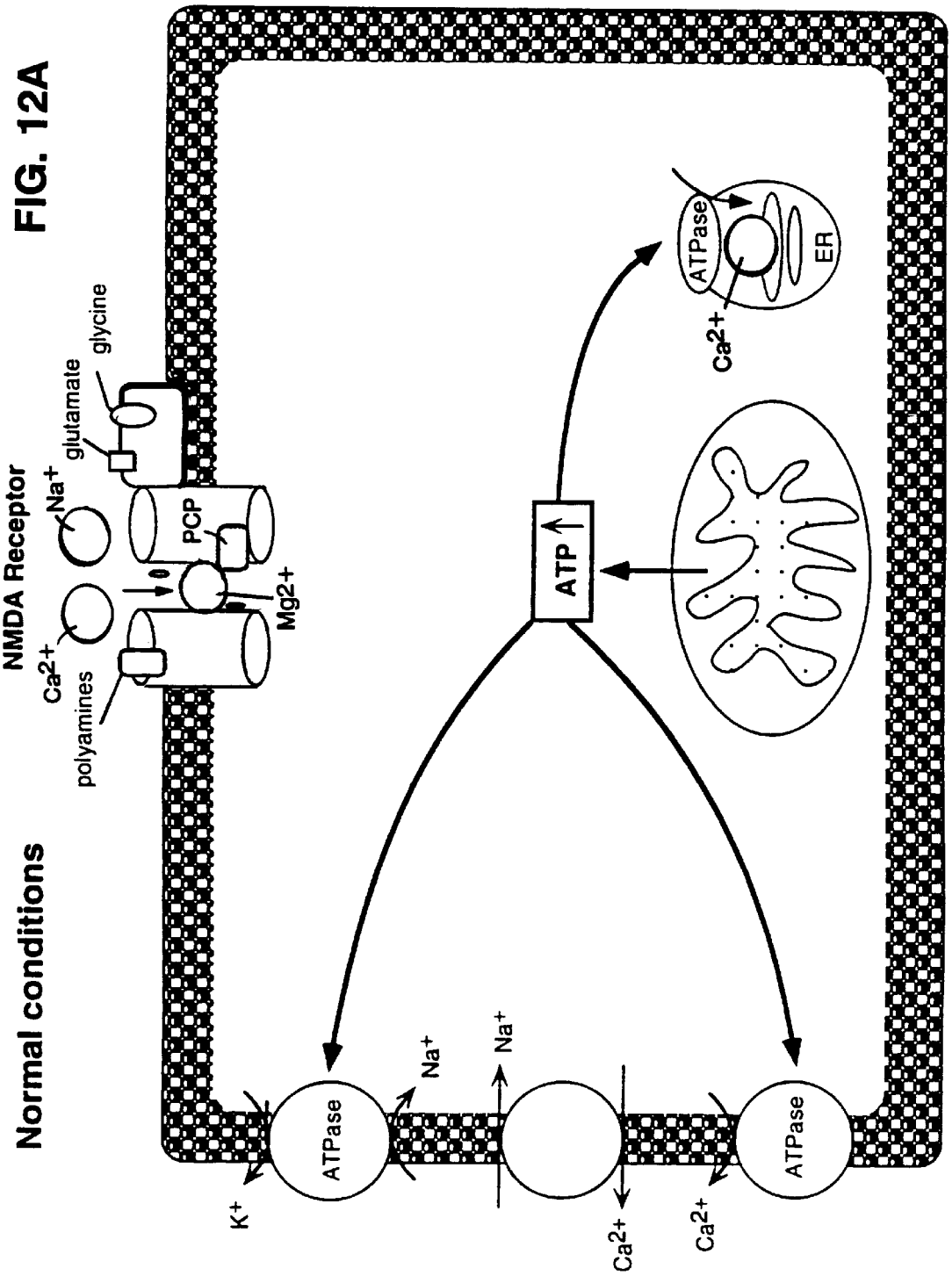

METHODS OF INHIBITING NEURODEGENERATIVE DISEASES

This is a continuation of application Ser. No. 08/372,302, filed Jan. 13, 1995, now abandoned.

STATEMENT AS TO FEDERALLY SPONSORED RESEARCH

This invention was made in part with Government funding and the Government may therefore have certain rights in the invention.

BACKGROUND OF THE INVENTION

This invention relates to the treatment of neurodegenerative diseases.

In human and nonhuman primates 1-methyl-4-phenyl1,2,3,6-tetrahydropyridine (MPTP) produces clinical, biochemical, neuropathologic changes analogous to those observed in idiopathic Parkinson's disease. The neurotoxic effects of MPTP are thought to be initiated by 1-methyl-4-phenylpyridinium (MPP+), which is a metabolite formed by the monoamine oxidase B-mediated (MAO-B) oxidation of MPTP (for review, see Tipton and Singer (1993) J. Neurochem. 61:1191–1206). MPP+ is selectively taken up by high-affinity dopamine and noradrenaline uptake systems and is subsequently accumulated within mitochondria of dopaminergic neurons. There it disrupts oxidative phosphorylation by inhibiting complex I of the mitochondrial electron transport chain (Gluck et al. (1994) J. Biol. Chem. 269:3167–3174). The interruption of oxidative phosphorylation results in decreased levels of ATP (Chan et al. (1991) J. Neurochem. 57:348–351), which may lead to partial neuronal depolarization and secondary activation of voltage-dependent NMDA receptors, resulting in excitotoxic neuronal cell death (Beal (1992) Ann. Neurol. 31:119–130). Although excitotoxic neuronal damage has been linked to $Ca^{2+}$ influx, the subsequent crucial steps that lead to cell death remain unknown.

The entry of calcium through N-methyl-D-aspartate (NMDA) receptor channels into cells stimulates nitric oxide synthase (NOS) activity by binding to calmodulin, a cofactor for NOS (Bredt and Snyder (1990) Proc. Natl. Acad. Sci. USA 87:682–685). Studies in dissociated cell cultures showed that NOS inhibitors blocked NMDA-induced cell death (Dawson et al. (1991) Proc. Natl. Acad. Sci. USA 88:6368–6371). NO˙ may react with superoxide ($O_2^-$) to generate peroxynitrite (Beckman et al. (1990) Proc. Natl. Acad. Sci. USA 87:1621–1624). Peroxynitrite has been identified as a potent oxidant (Beckman et al. (1992) Arch. Biochem. Biophys. 298:438–445; Ischiropoulos et al. (1992) Arch. Biochem. Biophys. 298:431–437), mediating the nitration of tyrosine and producing hydroxyl radicals (Beckman et al. (1990) supra; Crow et al. (1994) Free Radic. Biol. Med. 16:331–338; van der Vliet et al. (1994) FEBS Lett. 339:89–92). NOS has been implicated as having a role in focal ischemia (Huang et al. (1994) Science 265:1883–1885).

Recently, improved inhibitors of NOS have been described. 7-nitroindazole (7-NI) has been reported to be a potent and selective inhibitor of neuronal NOS in vitro and in vivo (Babbedge et al., (1993) Br. J. Pharmacol. 110:225–228; Moore et al. (1993) Br. J. Pharmacol. 110:219–224). Although in vitro studies suggest that 7-NI inhibits both endothelial and neuronal NOS, in vivo studies showed no effect on blood pressure and no effects on endothelium-dependent blood vessel relaxation and acetylcholine-induced vasodepressor effects (Babbedge et al. (1993) supra; Moore et al. (1993) supra, Wolff and Gribin (1994) Arch. Biochem. Biophys. 311:300–306). 7-NI has been shown to be efficacious against focal ischemic lesions in vivo (Yoshida et al. (1994) J. Cereb. Blood Flow Metab. 14:924–929).

SUMMARY OF THE INVENTION

The invention features treating neurodegenerative diseases by administration of a therapeutically effective amount of inhibitor of neuronal nitric oxide synthase, e.g., a nitroindazole such as 7-NI.

By the term "neurodegenerative disease" is meant any pathological state involving neuronal degeneration, including Parkinson's Disease, Huntington's Disease, Alzheimer's Disease, and amyotrophic lateral sclerosis (ALS).

By the term "therapeutically effective amount" as used herein means an amount sufficient to effect sufficient in vivo inhibition of a neuronal nitric oxide synthase to bring about clinical improvement in a human patient.

A therapeutically effective amount of nitroindazole may be prepared for administration to a patient in need thereof in a number of ways known to the art, including parental, intranasal, and oral formulations. Nitroindazole may also be formulated for implants. The concentration of nitroindazole in a physiologically acceptable formulation will vary depending on a number of factors, including the dosage to be administered, the route of administration, and the specific neurodegenerative condition being treated and its severity. The preferred dosage of nitroindazole will be determined by variables generally considered by the healthcare provider in determining dosages. Typical dosage of nitroindazole to be administered is from about 0.0001 mg nitroindazole/kg body weight to about 10 mg nitroindazole/kg body weight. Frequency of administration may vary from as frequently as daily to as infrequently as once every 1–2 weeks, or once every 6–8 weeks. Treatment will generally be continued as long as necessary to maintain inhibition of neuronal nitric oxide synthase and neuronal injury.

The inventors herein provide evidence that nitric oxide plays a role in in vivo neurotoxicity. Accordingly, in one embodiment, the invention features a method for treating nitric oxide-mediated pathological conditions by administration of a therapeutically effective amount of neuronal nitric oxide synthase inhibitor.

By "nitric oxide-mediated pathological condition" is meant a degenerative condition resulting at least in part from in vivo production of neuronal nitric oxide.

Other features and advantages of the invention will be apparent from the following preferred embodiments thereof, and from the claims.

DETAILED DESCRIPTION

Figure 1:
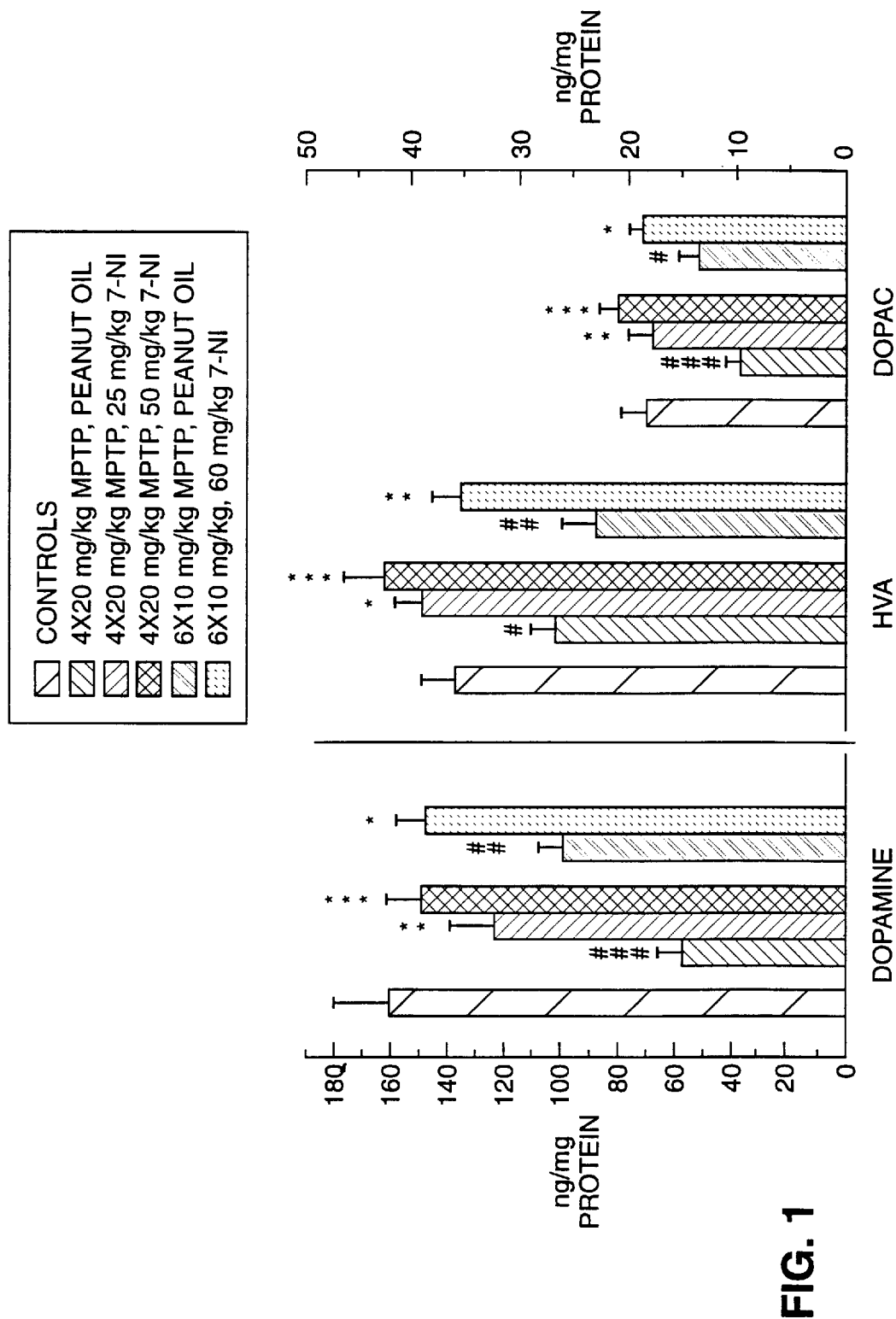
FIG. 1 shows the concentrations of dopamine, 3,4-dihydroxyphenylacetic acid (DOPAC), and homovanillic acid (HVA) controls or MPTP-treated animals receiving 0, 25 or 50 mg/kg 7-nitroindazole (7-NI), as described in Example 1 (mean±SEM; n=11–12). #=$p<0.05$, ##=$p<0.01$, and ###=$p<0.001$, *=$p<0.05$, =$p<0.001$, *=$p<0.001$ (ANOVA followed by Fisher PLSD post hoc test) (ANOVA).

The inventors have shown, for the first time, that inhibition of a neuronal isoform of NOS offers protection against neurotoxicity in vivo, and that blocking the activity of neuronal NOS with an NOS inhibitor provides protection against neurotoxicity in murine models of Parkinson's and Huntington's Diseases.

Example 1 below describes the inhibition of neuronal NOS by 7-nitroindazole (7-NI) resulting in in vivo protection against MPTP-induced neurotoxicity. These results show for the first time that treatment with 7-NI dose-dependently protects against MPTP-induced dopamine depletions in vitro. 7-NI was effective in two different dosing regimens of MPTP that produce varying degrees of dopamine depletion. At 50 mg/kg of 7-NI there was almost complete protection in both paradigms. Similar effects were seen with MPTP-induced depletions of both homovallinic acid (HVA) and 3,4-dihydroxyphenylacetic acid (DOPAC). These neuroprotective effects do not appear to be due to an inhibition of MAO-B activity, because 7-NI had no significant inhibitory effect on this enzyme either in vitro and in vivo. 7-NI also had no influence on dopamine uptake in vitro. Nor are the observed effects due to temperature; 7-NI produced only small changes in body temperature and showed the same degree of protection when the temperature of mice was maintained at 37.5° C.

These results therefore indicate that NO˙ plays a critical role in MPTP-induced neurotoxicity. One mechanism by which NO˙ may mediate toxicity is by interacting with superoxide radical to form peroxynitrite (ONOO⁻). Consistent with this hypothesis, MPTP neurotoxicity in mice resulted in a significant increase in the concentration of 3-nitrotyrosine, which was attenuated by treatment with 7-NI. These results also show the involvement of peroxynitrite in neurotoxicity.

In Example 2, the ability of 7-NI to block striatal lesions produced by direct acting and secondary excitotoxins was examined. Direct acting excitotoxins include N-methyl-D-aspartate (NMDA), kainic acid, and α-amino-3-hydroxy-5-methyl-4-isoxazolepropionic acid (AMPA). Secondary excitotoxic striatal lesions were produced by the reversible succinate dehydrogenase inhibitors malonate and the irreversible inhibitor 3-nitropropionic (3-NP). It has previously been found that both malonate and 3-NP produce striatal lesions by a secondary excitotoxic mechanism as a consequence of impaired energy metabolism (Beal et al. (1993) J. Neurochem. 61:1147–1150; Greene et al. (1993) J. Neurochem. 61:1151–1154; Henshaw et al. (1994) Brain Res. 647:161–166). The results described in Example 2 show that 7-NI significantly attenuated lesions produced by intrastriatal injections of NMDA, but not kainic acid or AMPA. 7-NI attenuated malonate lesions and resulted in nearly complete protection against striatal lesions produced by systemic administration of 3-NP. This is the first evidence that inhibition of neuronal NOS can attenuate striatal lesions produced by either intrastriatal administration of malonate or systemic administration of 3-nitropropionic acid (3-NP). 7-NI was much more effective against these secondary excitotoxic lesions than it was against the direct acting excitotoxin NMDA.

To evaluate the mechanism of neuroprotection, we investigated the in vivo effects of 7-NI on spontaneous striatal electrophysiological activity in rat striatum. In contrast to the NMDA antagonist MK-801, which inhibited electrophysiological activity, 7-NI had no significant effects, suggesting that it is not acting at NMDA receptors. The ability of 7-NI to attenuate ATP depletions and increases in lactate concentrations produced by intrastriatal administration of malonate was examined. 7-NI protected both against malonate-induced decreases in ATP, and increases in lactate, as assessed by chemical shift magnetic resonance spectroscopy. This result contrasts with those of a free radical spin trap which exerts neuroprotective effects but had no effect on malonate-induced depletions of ATP (Schulz et al. (1995) 64:in press). Similarly, MK-801 which has neuroprotective effects against 3-NP-induced neurotoxicity in vitro had no effect on ATP depletions (Riepe et al. (1994) NeuroReport 5:2130–2132).

The effect of 7-NI on 2,3 dihydroxybenzoic acid (DHBA) and 3-nitrotyrosine were also investigated. Hydroxyl radical generation results in an increase in the conversion of salicylate to 2,3 DHBA (Floyd et al. (1984) J. Biochem. Biophys. Methods 10:221–235; Hall et al. (1993) J. Neurochem. 60:588–594). As is shown in Example 2, 3-NP produced an increase in 2,3 DHBA/salicylate, which is attenuated by pretreatment with 7-NI. 3-NP also induced increases in 3-nitrotyrosine, which was also attenuated by prior treatment with 7-NI. These results suggest that peroxynitrite may play a role in 3-NP-induced neurotoxicity in vivo.

Figure 12B:
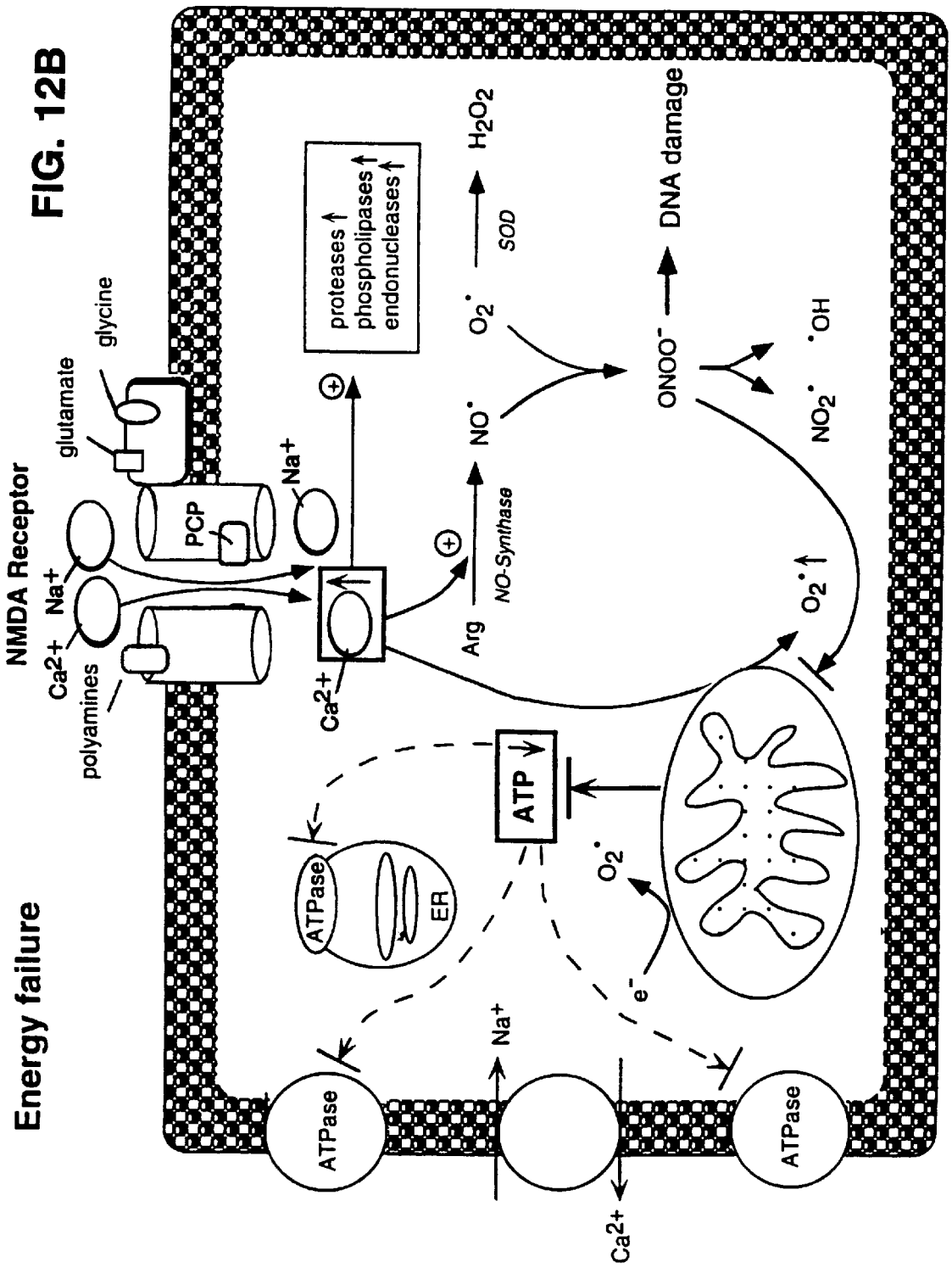
FIG. 12 is a schematic representation of the NMDA receptor mediated cascade of cell death and potential steps of therapeutic intervention.

A mechanism of NMDA receptor mediated cascade of cell death and potential steps of therapeutic intervention are illustrated in FIG. 12. The upper panel of FIG. 12 shows how mitochondria provide ATP that fuels a multitude of ion pumps which produce and maintain voltage and ion gradients across neuronal membranes, thereby creating a resting potential of −80 mV. The cytoplasmic $Ca^{2+}$ concentration is maintained several orders of magnitude lower than outside the cell by means of ATPases that actively move $Ca^{2+}$ out of the cell or into intracellular storage organelles such as the endoplasmic reticulum (ER). The lower panel of FIG. 12 illustrates how excitotoxicity may occur as a consequence of a defect in energy metabolism. This mechanism may be due to membrane depolarization due to ATP depletion, followed by relief of the voltage dependent $Mg^{2+}$ block of the NMDA receptor, leading to an ion influx, especially the inward movement of $Na^+$ and $Ca^{2+}$. The intracellular $Ca^{2+}$ concentration increases dramatically leading to an activation of $Ca^{2+}$ dependent enzymes, including neuronal NOS which produces $NO^·$. $NO^·$ may interact with superoxide radicals ($O_2^·$) to form peroxynitrite $(ONOO^-)^8$. The formation of peroxynitrite does not require transition metals, and once formed it can diffuse over several cell diameters where it can oxidize lipids, proteins and DNA. It also can produce nitronium ions which then nitrate tyrosine residues. Peroxynitrite can also be protonated to form ONOOH which may then decompose to $OH^·$. $NO^·$ can inhibit cytochrome oxidase in vitro and de-energizes mitochondria, thereby leading to an additional decline in mitochondrial function. Increased mitochondrial $Ca^{2+}$ concentrations also lead to an increase in $OH^·$ (Dykens (1994) J. Neurochem. 63:584–591). The block of the electron flux through the electron transport chain produces $O_2^·$.

We provide herein evidence that $NO^·$ plays a role in NMDA, malonate and 3-NP neurotoxicity in vivo. This evidence provides an important new insight for the treatment of neurodegenerative disease such as Parkinson's disease, Huntington's disease, Alzheimer's disease, amyotrophic lateral sclerosis, and other neurodegenerative diseases which are mediated by $NO^·$.

Without further elaboration, it is believed that one skilled in the art can, using the preceding description, utilize the instant invention to its fullest extent. Accordingly, the following experimental examples are illustrative and by no means intended to limit the scope of the claimed invention.

EXAMPLE I

Inhibiting of Neuronal Nitric Oxide Synthase BV 7-Nitroindazole Protects Against MPTP-Induced Neurotoxicity in Mice.

Methods. Male Swiss-Webster mice (30–35 g:Taconic Farms, Germantown, N.Y., U.S.A.) were treated with either normal saline or MPTP hydrochloride (Research Biochemicals, Natick, Mass., U.S.A.). MPTP was administered in 0.1 ml of water at a dose of 10 mg/kg i.p. at 2-h intervals for six doses or 20 mg/kg i.p. at 2-h intervals for four doses. 7-NI (Cookson Chemical Ltd., Southhampton, U.K.) was dissolved in peanut oil (Sigma, St. Louis, Mo., U.S.A.) at a concentration of 5 mg/ml. Mice received doses of 25 or 50 mg/kg per subcutaneous injection. MPTP-treated animals were treated with peanut oil or 7-NI 12 h before the first, at every MPTP injection, and every 8 h for 48 h after MPTP injections. Eleven to 12 animals were used in each group. Animals were killed at 1 week. The two striata were rapidly dissected and placed in chilled 0.1M perchloric acid. Tissue was subsequently sonicated, and aliquots were taken for protein quantification using a fluorometric assay (Beal et al., 1990) J. Neurochem. 55:1327–1339).

Dopamine, 3,4-dihydroxyphenlyacetic acid (DOPAC), homovanillic acid (HVA), p-tyrosine, and 3-nitrotyrosine were quantified by HPLC with 16-electrode electrochemical detection (Beal et al. (1990) supra) and are expressed as ng/mg protein (mean±SEM) (FIG. 1). 3-Nitrotyrosine data are expressed as ratios of 3-nitrotyrosine to p-tyrosine to normalize for differing brain concentrations of tyrosine. The statistical significance of differences was determined via one-way ANOVA followed by Fisher PLSD post hoc test to compare group means. All animal use procedures were in strict accordance with the NIH *Guide for the Care and Use of Laboratory Animals* and were approved by the local Animal Care Committee.

The effect of 7-NI on MAO-B activity was studied. Mice (six per group) were treated at 2-h intervals for four doses of peanut oil (vehicle) s.c., 10 mg/kg of deprenyl i.p. dissolved in 0.9% phosphate-buffered saline, or 50 mg/kg of 7-NI s.c. dissolved in peanut oil. The mice were killed 1 h after the last injection. Crude mitochondrial preparations were obtain from the forebrains by applying the $P_2$ pellet to a discontinuous Ficoll gradient. The MAO-B activity in the mitochondrial fractions was determined spectrophotometrically by measuring the rate of deprenyl-sensitive oxidation of benzylamine to benzaldehyde (Tabor et al. (1954) J. Biol. Chem. 208:645–651; Krueger and Singer (1993) Anal. Biochem. 214:116–123). The same assay was performed in vitro in the presence or absence of 7-NI in the mitochondrial fraction of mouse forebrain tissue.

The ability of 7-NI to inhibit the dopamine transporter was tested with an in vitro assay for [$^3$H] dopamine uptake into striatal mouse synaptosomes (Javitch et al. (1985) Proc. Natl. Acad. Sci. USA 82:2173–2177). In our system dopamine uptake was saturable with half-maximal uptake at 60 nM and a $V_{max}$ value of 2.2 nmol/g of tissue/min. For the inhibition studies with 7-NI, we used 0.13 μM [$^3$H]-dopamine as substrate and 10 μM mazindol to block the specific binding.

Role of Peroxynitrite in MPTP. To determine whether peroxynitrite plays a role in MPTP neurotoxicity, we therefore measured the ratio of 3-nitrotyrosine to tyrosine in mouse striatum following administration of MPTP.

RESULTS

Six doses of 10 mg/kg MPTP at 2-h intervals produced a 38% depletion in dopamine levels, whereas DOPAC and HVA levels were depleted by 27 and 35%, respectively, at 1 week (FIG. 1). Treatment with 50 mg/kg 7-NI almost completely (92% of control values) blocked the MPTP-induced dopamine depletions. Subsequently the efficacy of 7-NI treatment in MPTP toxicity was confirmed by a more severe dosing regimen with four doses of MPTP of 20 mg/kg: At 1 week dopamine was depleted by 64%, DOPAC, with inducted depletions of dopamine, HVA, and DOPAC, with almost complete protection with a dose of 50 mg/kg (FIG. 1). Rectal temperature measurements in 10 7-NI (50 mg/kg)-treated mice as compared with 10 peanut oil controls shows no significant decrease at 1 h but a significant 0.6° C. decrease at 0.5 h after the injection (36.2±0.1 vs. 36.8±0.2° C.; p=0.03). To exclude the possibility that hypothermia may contribute to the protection, we maintained body temperature at 37.5° C. in controls, mice treated with four doses of MPTP at 20 mg/kg, and mice additionally treated with 7-NI (n=6 per group). Under these conditions the protection by 7-NI was almost complete [dopamine values; controls, 142.1±5.0 ng/mg of protein; MPTP-treated, 17.1±2.6 ng/mg (p<0.001 compared with controls and 7-NI-treated group); MPTP- and 7-NI-treated, 133.1±6.5 ng/mg].

Figure 2:
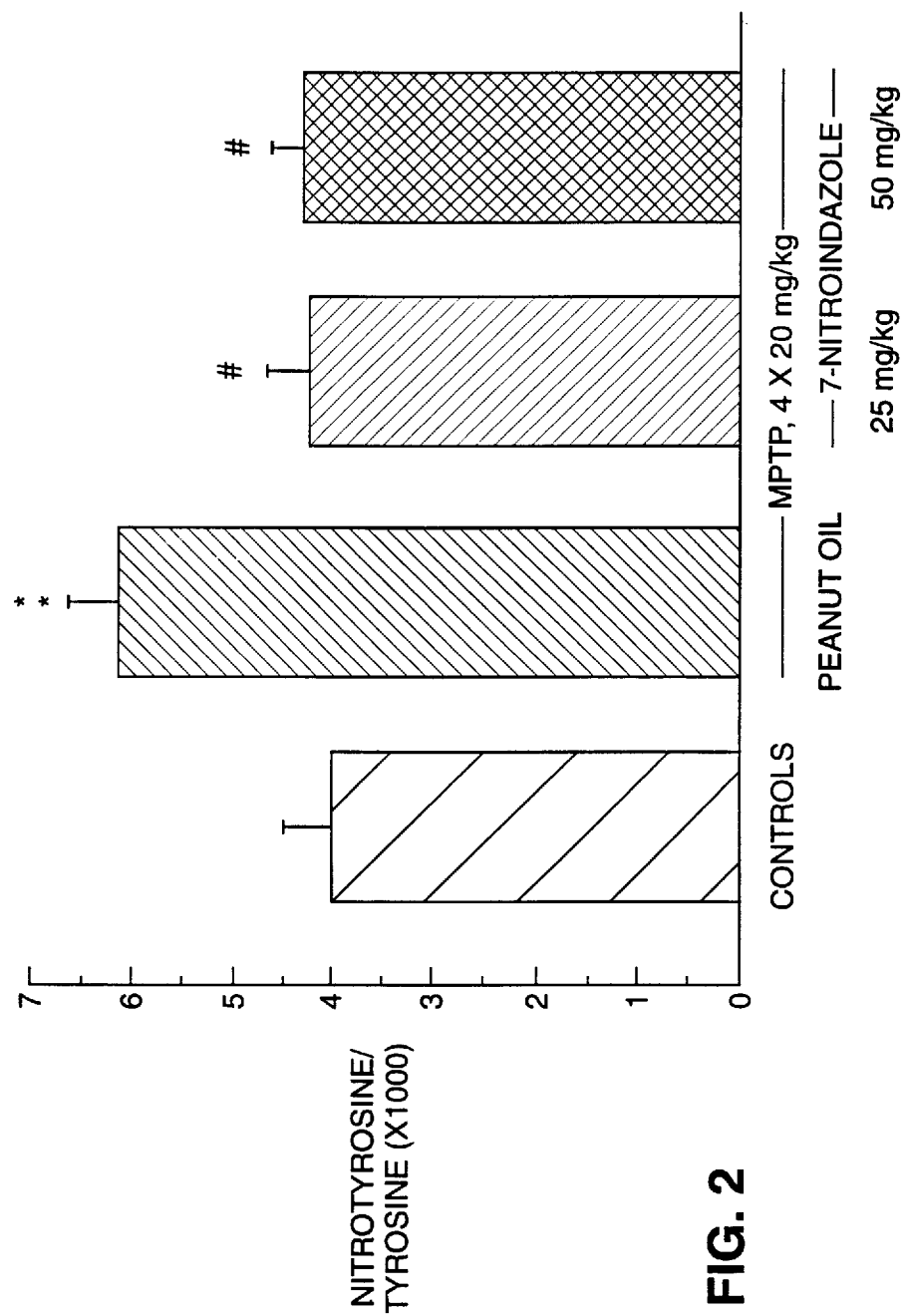
FIG. 2 shows the effect of MPTP treatment on the formation of 3-nitrotyrosine in mouse striatum and mice additionally treat with 7-NI (mean±SEM; n=11–12). **=$p<0.001$, #=$p<0.005$ (ANOVA).

Peroxynitrite, a product of NO· reaction with $O_2^-$ mediates the nitration of tyrosine (Beckman et al. (1992) supra; Ischiropoulos et al. (1992) supra). 3-Nitrotyrosine was quantified by HPLC with electrochemical detection. Its maximal oxidation potential was 840 mV, with a retention time of 24 minutes. Reaction of standard and samples with 1M-sodium hydrosulfide (dithionite) completely abolished the 3-nitrotyrosine peaks by conversion of 3-nitrotyrosine to aminotyrosine. The control levels for tyrosine and 3-nitrotyrosine were 488.9±34.0 and 2.0±0.1 ng/mg of protein, respectively. In mice that received four doses of 20 mg/kg MPTP the ratio of 3-nitrotyrosine to tyrosine was significantly increased by 31% (FIG. 2). Administration of 25 or 50 mg/kg 7-NI significantly attenuated this increase in MPTP-treated mice. The 3-nitrotyrosine values of these mice did not differ significantly from controls. Deprenyl treatment reduced the MAO-B activity from 5.79±0.44 to 0.22±0.22 nmol/min/mg of protein (p<0.001). In contrast to this finding treatment with 7-NI had no influence on MAOB activity (5.69±0.40 nmol/min/mg of protein). In vitro 7-NI at 1, 10, and 100 $\mu$M did not inhibit MAO-B activity. The $K_1$ of deprenyl was 0.3 $\mu$M with complete inhibition at 1.2 $\mu$M. 7-NI at 1, 10 and 100 $\mu$M did not inhibit the [$^3$H] dopamine uptake into synaptosomes in vitro, whereas the $K_1$ of mazindol was 0.05 $\mu$M with complete inhibition at 1 $\mu$M.

MPTP treatment resulted in a significant increase in the 3-nitrotyrosine to tyrosine ratio, which was attenuated by 25 or 50 mg/kg of 7-NI. These findings are therefore consistent with a role of peroxynitrite in MPTP neurotoxicity.

EXAMPLE II

Striated Lesions Produced by N-Methyl-D-Aspartate, Malonate, and 3-Nitropropionic Acid are Attenuated By Nitroindazole.

Methods and Materials

Chemicals. Malonate, N-methyl-D-aspartate (NMDA), kainic acid (KA), and peanut oil were obtained from Sigma (St. Louis, Mo.), α-amino-3-hydroxy-5-methylisoxazole-4-propionic acid (AMPA) from Research Biochemicals (Natick, Mass.), 3-nitropropionic acid (3-NP) from Aldrich (Milwaukee, Wis.) and 7-NI from Cookson Chemical Ltd. (Southhampton, UK).

Stereotaxic Lesion Technique. Male Sprague-Dawley rats (Charles River, Cambridge, Mass.) weighing 300–325 g were anesthetized with pentobarbital (50 mg/kg i.p.) and positioned in a David Kopf stereotaxic instrument with the incisor bar set at 3.3 mm below the intermural line. Malonate, NMDA, KA, and AMPA were dissolved in 0.1M phosphate-buffered saline (pH, 7.4). Intrastriatal injections were made with a 10 $\mu$l Hamilton syringe fitted with a 30 gauge blunt-tipped needle into the left striatum at the coordinates 0.5 mm anterior bregma, 2.6 mm lateral to the midline and 5 mm ventral to the dura. Injection volumes were 1 $\mu$l (3 $\mu$mol malonate). All injections were made over 1 min and the needle was left in place for an additional 1 min before being slowly withdrawn. 7-NI was dissolved and sonicated in peanut oil at a concentration of 10 mg/ml. 50 mg/kg of 7-NI were administered i.p. 30 min before striatal injections of malonate, NMDA, KA and AMPA. Since this paradigm did not show any protective effects for NMDA, KA, and AMPA injections as compared to controls, a second experiment was conducted in which two doses of 50 mg/kg of 7-NI were administered i.p. at 4 h and 0.5 h before striatal injections of NMDA, KA, and AMPA. Initial results showed that 7-NI significantly decreased body temperature in rats under pentobarbital anesthesia measured 1 h after administration of 50 mg/kg 7-NI i.p. (35.9±0.26° c. versus 36.5±0.1° C., n=10, p<0.02). Since hypothermia may produce neuroprotection, the body temperature of the animals was maintained at 37.5° C. in an incubator as long as the rats were anesthetized. Nine to ten animals were used per group in each experiment.

Quantification of Lesion Volume. One week after the striatal injections, animals were sacrificed by decapitation and the brains were rapidly removed, placed in cold saline for 10 min, and sectioned coronally into slices at 2 mm intervals. Slices were stained in 2% 2,3,5-triphenyltetrazolium chloride monohydrate (TTC) (Sigma, St. Louis, Mo.) solution at room temperature in the dark for 30 min followed by fixation in phosphate-buffered 4% paraformaldehyde. (Bederson et al. (1986) Stroke 17:1304–1308.) The lesioned area (noted by pale staining) was measured on the posterior surface of each section using an Apple Macintosh© based image analysis system (Sony color video camera, Software: ColorSnap© (Computer Friends Inc., Portland, Oreg.) and IPLab Spectrum© (Signal Analytics, Vienna, Va.)). The lesions were evaluated by an experienced histologist, who verified the reliability of the TTC measurements in animals injected with malonate on adjacent sections stained with either TTC or Nissl stain (Schulz et al. (1995) J. Neurochem 64:in press).

Systemic 3-NP treatment. 3-NP was diluted in water and adjusted to pH 7.4 with NaOH and administered at a dose of 10 mg/kg i.p. every 12 h. With this dosing regimen the animals become acutely ill after 4 to 5 days and show large striatal lesions. (Beal et al. (1993) J. Neurosci. 13:4181–4192.) At the same time points, 25 mg/kg of 7-NI dissolved in peanut oil at a concentration of 10 mg/ml (treated group) or vehicle alone (peanut oil, control group) was administered s.c.. Since there was variability in the times at which animals became ill, they were clinically examined 3 hours after the injections and 1 animal of each group was sacrificed when an animal was acutely ill, regardless of whether it was a vehicle treated control or a 7-NI treated animal. In an initial experiment 12 animals per group were studied. Following sacrifice, striatal lesion size was assessed by TTC staining.

In a second experiment, 5 animals per group were studied with the same treatment paradigm. Since the first experiment had shown by pairwise sacrifice that the vehicle treated animals always became ill before the 7-NI treated animals, a third experimental group of 5 animals was included to determine whether 7-NI treated animals become ill following administration of 3-NP. These animals were treated with 3-NP and 7-NI identically to animals of the other 7-NI treated group, but were not sacrificed when vehicle treated animals became ill but only later, when they showed symptoms. In this experiment animals were deeply anesthetized and transcardially perfused with ice cold saline, followed by phosphate buffered 4% paraformaldehyde (Beal et al. (1991) J. Neurosci. 11:1649–1659). Brains were sectioned at 50 $\mu$m intervals on a freezing microtome. Combined staining for Nissl substance and NADPH-diaphorase was performed. Adjacent sections were stained by immunohistochemistry with antibodies against $^8$-hydroxy-2deoxyguanosine.

Salicylate assay and 3-nitrotyrosine measurements. The salicylate hydroxyl trapping method of Floyd et al. ((1984) supra, Cao et al. (1988) Neurosci. Lett. 88:233–238, and Hall et al. (1993) J. Neurochem. 60:588–594) was used for measuring ˙OH radicals in striatal tissue following i.p. administration of 3-NP. Male Sprague Dawley rats weighing 125–150 g (n-10 per group) were injected i.p. every 12 h for 3 times with either (i) saline, (ii) 20 mg/kg of 3-NP and peanut oil vehicle, or (iii) 20 mg/kg of 3-NP and 7-NI dissolved in peanut oil. 1.5 h after the last injection of 3-NP or saline salicylate (150 mg/kg) was administered i.p. One hour later the animals were sacrificed and the right and left striata were rapidly dissected from a 2-mm-thick slice on a chilled glass plate, and placed in 0.5 ml chilled 0.1M PCA. The samples were sonicated, rapidly frozen, thawed and centrifuged twice. Aliquots of the supernatant were stored at −70° C. until the time of assay. Salicylate and its metabolites 2,3 and 2,5 dihydroxybenzoic acid (DHBA) were quantified by HPLC with 16-electrode electrochemical detection (Beal et al. (1990) supra). Salicylate, 2,3 and 2,5 DHBA, tyrosine and 3-nitrotyrosine were measured electrochemically by oxidation at 840, 240, 120 mV, 600 mV, and 840 mV, respectively. The data were expressed as the ratio of 2,3 and 2,5 DHBA to salicylate and 3-nitrotyrosine concentrations for differing brain concentrations of salicylate and tyrosine, which could be a consequence of impairment of the blood-brain barrier (salicylate) or neuronal loss during treatment (tyrosine).

ATP Measurements. The effects of 7-NI on malonate-induced decreases in striatal ATP concentrations were examined. 50 mg/kg of 7-NI dissolved in peanut oil or peanut oil vehicle were administered i.p. 0.5 h before intrastriatal injection of 3 μmol malonate. At 3 h rats were deeply anaesthetized and the skull surface was exposed. After decapitation the heads were rapidly frozen in liquid nitrogen and subsequently stored at −70° C. The striata were dissected from a 2 mm slice frontal and adjacent to the anterior commissure on a freezing cold plate. The corpus callosum, the septal complex, and the anterior commissure were used as dorsal and lateral, medial, and ventral boundaries. ATP was measured by the luciferin-luciferase assay (Lust et al. (1981) Anal. Biochem. 110–258–266). Proteins were measured on the pellets using a fluorimetric assay. Eight animals per group were examined.

Localized Lactate Measurements by Magnetic Resonance Spectroscopy. The effects on lactate production of intrastriatal injections of 3 μmol malonate and the influence of pretreatment with 7-NI on these lactate levels were assessed in vivo using magnetic resonance imaging (Brouillet et al. (1993) J. Neurochem. 60:356–359). Male Sprague-Dawley rats weighing 275–325 g received either i.p. injections of peanut oil (vehicle) or 50 mg/kg 7-NI (n=5–6 per group). One h later striatal injections of malonate were performed as described above using halothane anesthesia. Rats were imaged under halothane/$N_2O/O_2$ anesthesia on a 4.7 Tesla GE Omega CSI Imager using a 30 mm bird cage coil at 1.5–2 h after striatal malonate injections. Animals were maintained at normal body temperature by use of a temperature regulated circulating water blanket placed on the body of the animal. Lesion volumes were measured using a $T_2$-weighted sequence (TR/TE 3200/80 ms) with slice thickness of 2.5 mm, and a field of view of 40 mm. Lesion volumes were measured using a criterion for abnormal tissue of being 2 standard deviations above the mean signal intensity in the contralateral unaffected striatum. Lactate was measured using double phase encoding three dimensional (x,y,ω) water suppressed chemical shift imaging sequence with an inversion pulse for lipid suppression described earlier (Jenkins et al. (1993) Neurology 43:2689–2695). Parameters were TR/TE/TI=2200/272/208 ms, with a field of view of 35 mm, 16×16 phase encode steps and a slice thickness of 8 mm. Lactate concentrations were measured in the lesioned striatum by delineating the striatum in the water image and overlaying the contours on the lactate images. The difference between the contralateral (unaffected) and lesioned striata was measured and then normalized to the N-acetylaspartate (NAA) signal intensity in the contralateral striatum, which was assumed to be 7 mM in concentration (Birken et al. (1989) Neurosci. Biobehav. Rev. 4:7–18 and references therein).

Electrophysiology. Four male Sprague-Dawley rats weighing 300 to 400 g were used for electrophysiological studies. Animals were anesthetized with urethane 1.5 g/kg i.p. and placed in a stereotaxic apparatus with their body temperatures maintained at 37° C. by a feedback heating pad. A 0.5×0.5 cm craniotomy was made and recording electrodes were placed in the anterior striatum using stereotaxic coordinates and aural monitoring. Following electrode placement the craniotomy was covered with 4% agar in saline and 30 min were allowed for stabilization before recordings were made. The spontaneous activity of multiple units were recorded extracellularly in the striatum, 3–4 mm anterior to the bregma and 3–4 mm lateral to the midline at a depth of 2.5–4.0 mm using commercially available tungsten microelectrodes (4 MΩ at 1 kHz, F. Haer, Inc.). The neuronal activity was amplified, broadcast with an audio monitor displayed on an oscilloscope and recorded with a desktop computer. Data acquisition and analysis of mean firing rate was performed using Discovery©, Experimenters WorkBench© and Personal Scientific Workstation© software (DataWave Technologies, Longmont, Colo.). We investigated the electrophysiological effects of the NMDA antagonist MK-801 and the NOS inhibitor 7-NI. Initially, baseline spontaneous activity was collected over a 20 minute period for 1 second every 19 seconds (60 samples). The animal was then given a s.c. injection of 50 mg/kg 7-NI. After 60 minutes, an additional 20 minutes of spontaneous neuronal activity was collected from the same recording site in the same manner. Finally, spontaneous activity was recorded after the NMDA channel mediated activity was blocked by injection of MK-801 (4 mg/kg).

Statistical Methods. Data are expressed as means±SEM values. Side-to-side comparisons were made by two-tailed paired t-test. The statistical significance of differences in lesion volume, DHBA and nitrotyrosine values, lactate production and ATP depletion between groups were determined by un paired Student's t-test (two tailed) or one-way analysis of variances (ANOVA) followed by Fisher's PLSD (protected least significant difference) post-hoc test to compare group means. The number of animals showing striatal lesions after systemic 3-NP treatment were compared by $\chi^2$ test.

RESULTS

Figure 3:
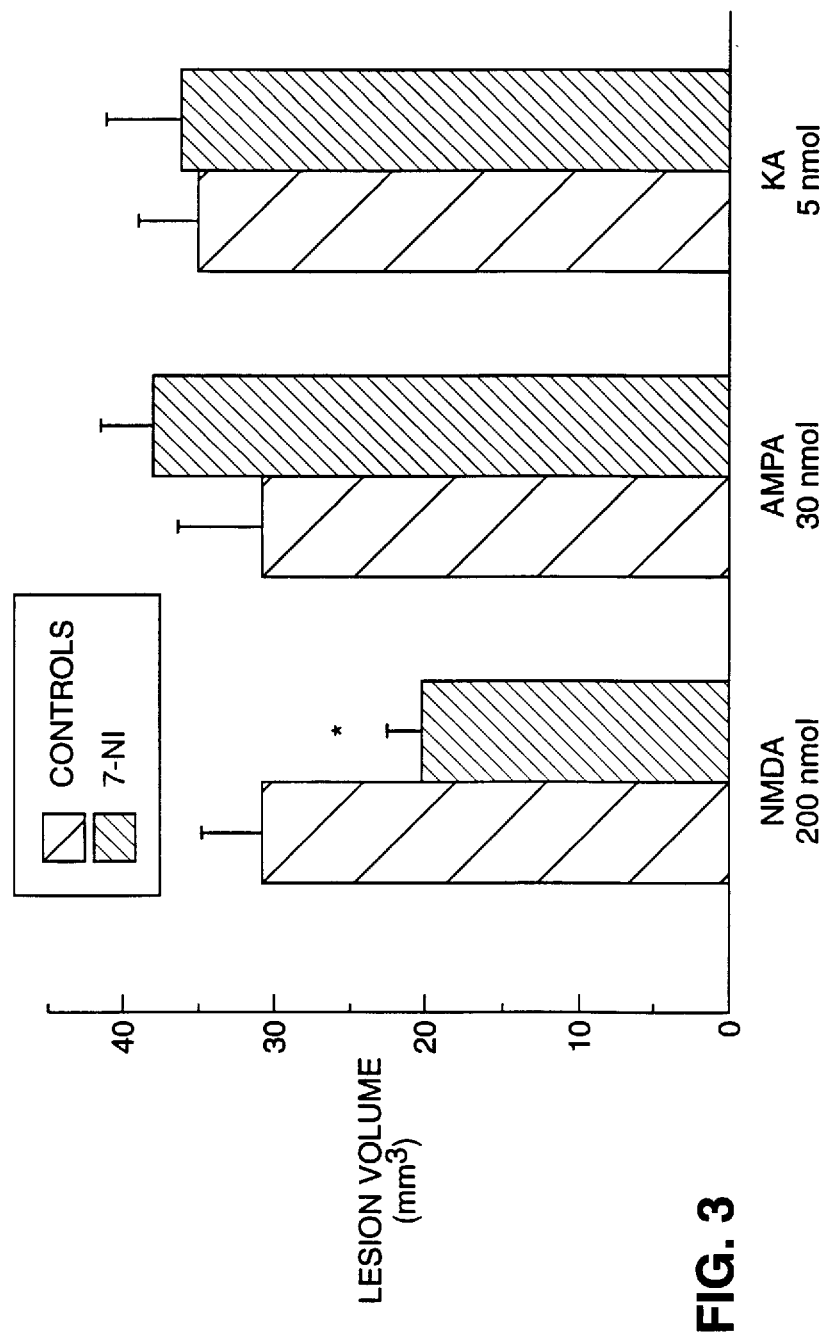
FIG. 3 shows the effect of pretreatment with 7-NI on striatal lesions produced by NMDA, AMPA and KA. *=p<0.05; n=9–10 (Student's t-test).

We examined whether pretreatment with the neuronal NOS inhibitor 7-NI can attenuate striatal excitotoxic lesions produced by the direct acting excitatory amino acid receptor agonists NMDA AMPA and KA. The experiments showed that a single dose of 7-NI (50 mg/kg i.p.) administered i.p. 1 h before striatal injections produced no protection (200 nmol NMDA 25.0±2.4 mm3 versus 21.3±3.4 mm$^3$ (vehicle versus 7-NI treatment); 30 nmol AMPA 33.6±4.6 mm$^3$ versus 30.4±5.2 mm$^3$; $^5$ nmol KA 39.5±2.9 mm$^3$ versus 36.3±4.4 mm$^3$; n=9–10). As shown in FIG. 3, treatment with 2 doses of 50 mg/kg 7-NI 4 h and 0.5 h before the striatal injection of the excitotoxins provided significant protection against lesions produced by 200 nmol NMDA (35%), but no protection against lesions produced by 30 nmol AMPA or 5 nmol KA.

Figure 4:
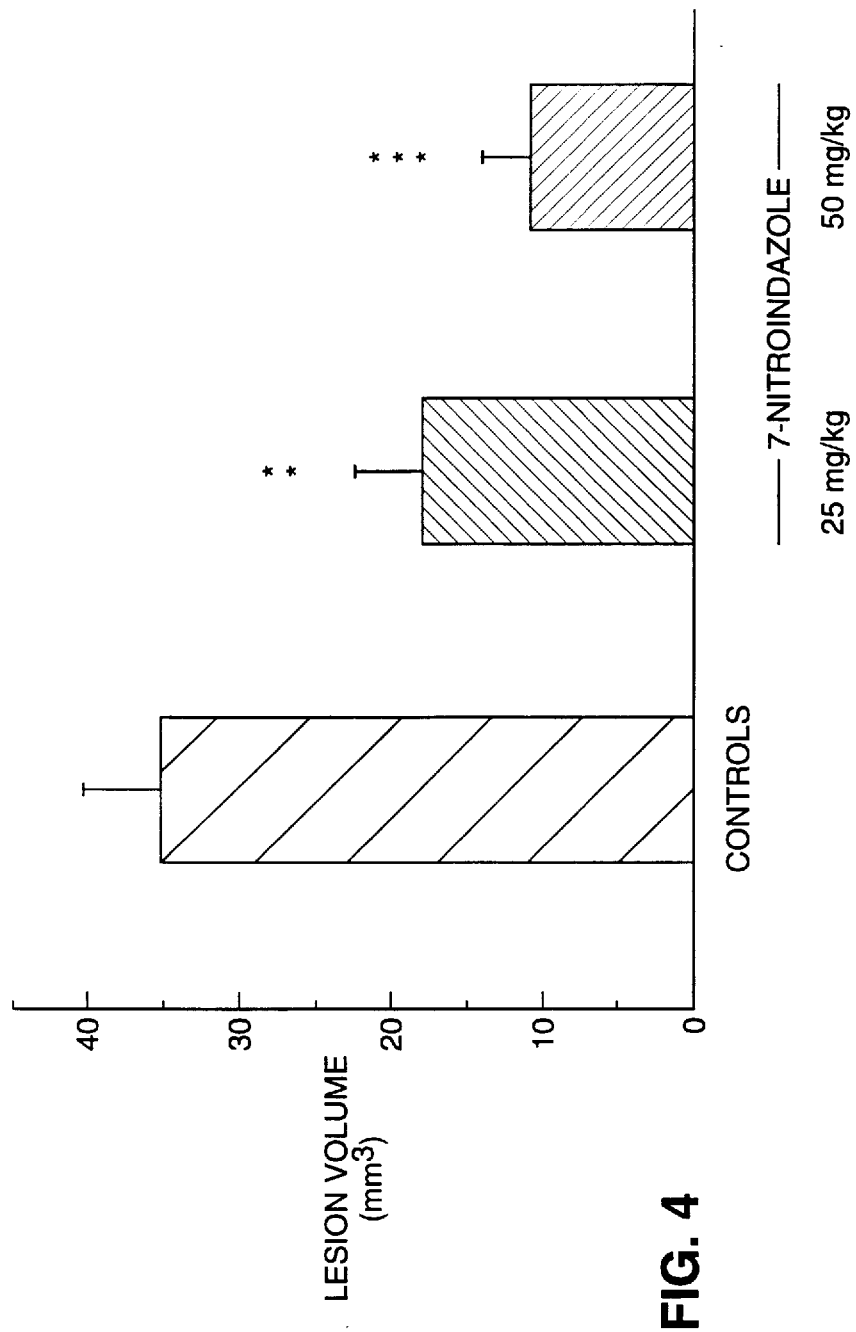
FIG. 4 shows the effects of pretreatment with 7-NI on striatal lesions produced by 3 μmol malonate. =p<0.01, *=p<0.001; n=10 (ANOVA).

Malonate, a reversible inhibitor of succinate dehydrogenase, has been reported to produce secondary excitotoxic lesions in the striatum (Beal et al. (1993) supra; Greene et al. (1993) supra; Henshaw et al. (1994) supra). Malonate produces ATP depletions and striatal lesions which are blocked by both competitive and non-competitive NMDA antagonists. We examined the effects of both 25 mg/kg and 50 mg/kg 7-NI administered i.p. 0.5 h before striatal injections of 3 $\mu$mol malonate. 7-NI significantly and dose dependently attenuated the striatal lesion produced by 3 $\mu$mol malonate (FIG. 4).

Figure 5:
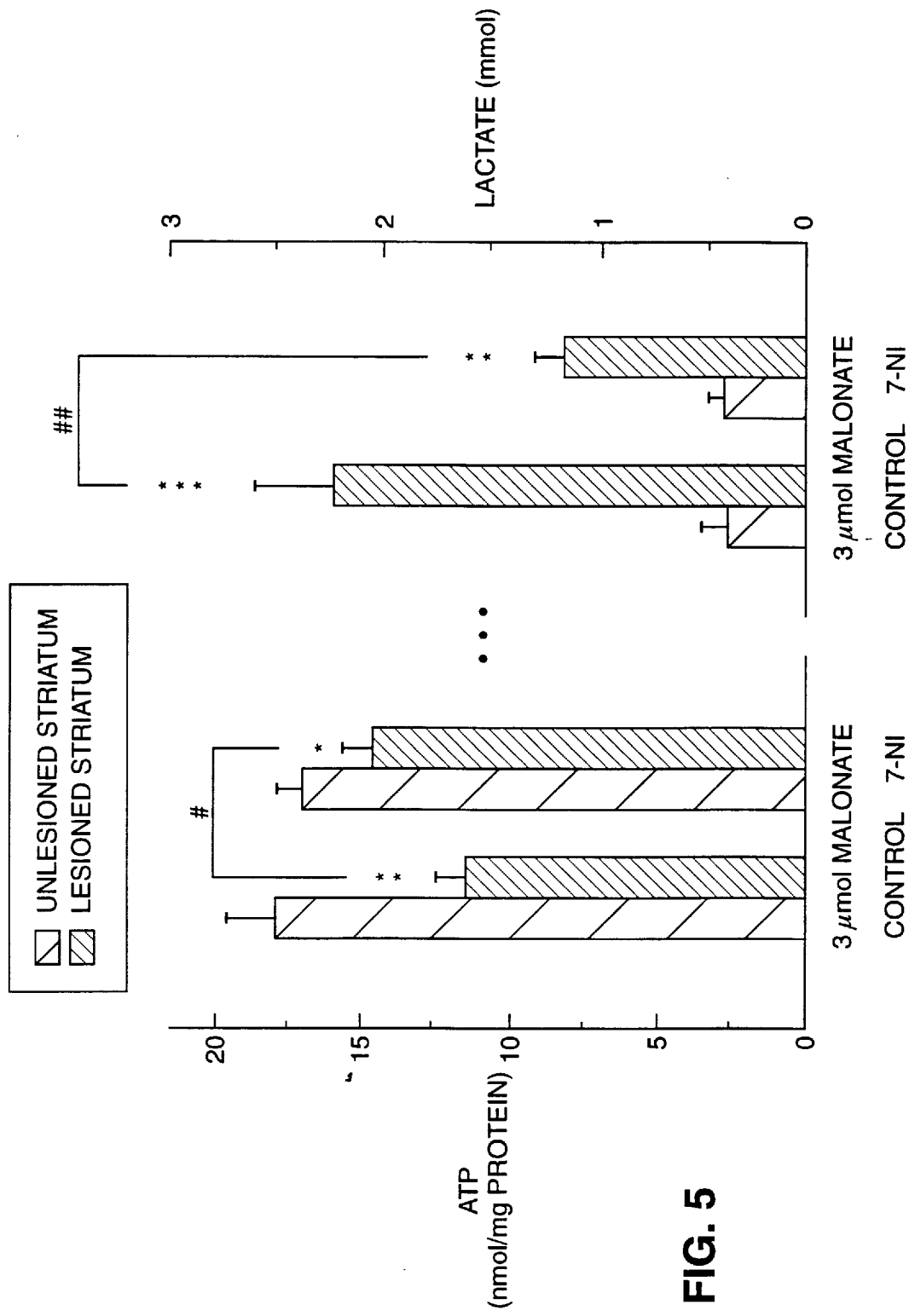
FIG. 5 shows the effects of pretreatment with 7-NI on ATP and lactate concentrations. *=p<0.05, =p<0.01, *=p<0.001 (paired Student's t-test), #=p<0.05, ##=p<0.01 (unpaired Student's t-test).
Figure 6A:
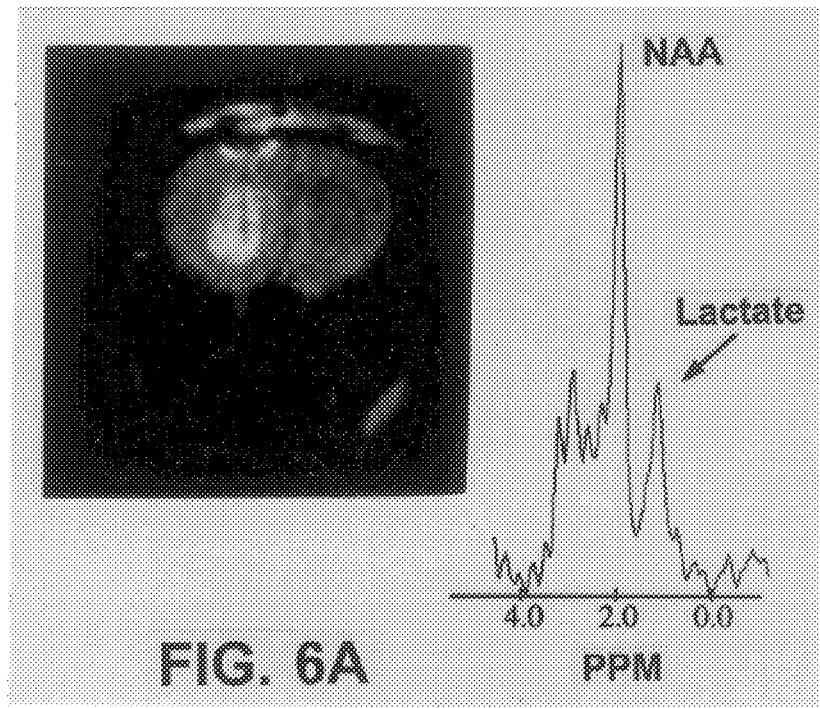
FIG. 6 shows the $T_2$-weighted images and striatal proton spectra in a rat 1.5 h after striatal injection of 3 μmol malonate without (upper panel) and with pretreatment of 50 mg/kg of 7-NI. NAA=N-acetylaspartate, PPM=parts per million.
Figure 6B:
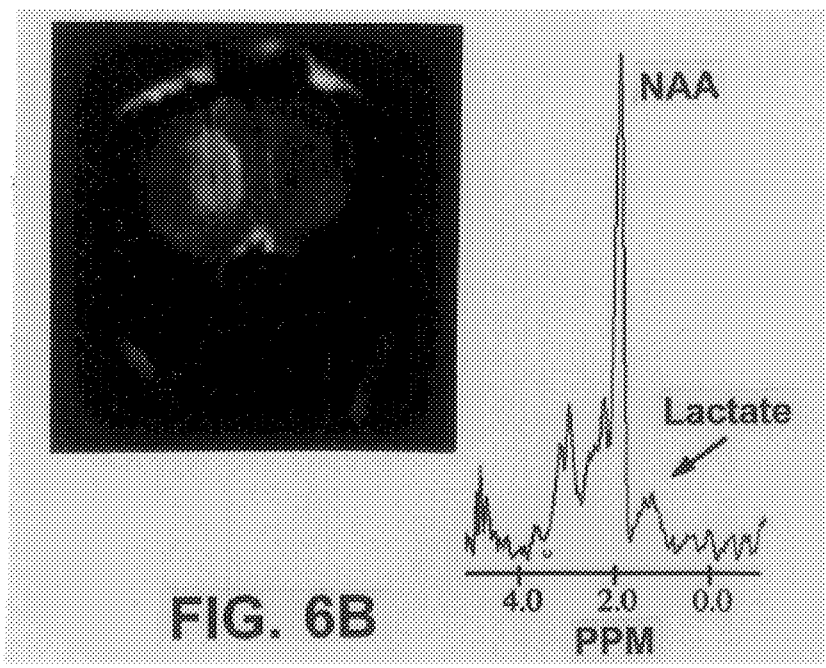

As compared to vehicle treated controls pretreatment with 50 mg/kg of 7-NI significantly attenuated decreases of striatal ATP concentrations measured 1.5 h after injections of 3 $\mu$mol of malonate (FIG. 5). Localized lactate concentrations were measured in vivo by using chemical shift MR spectroscopy. There is a profound increase in lactate production 1.5 h after striatal injection of malonate compared to the contralateral, unlesioned striatum (FIG. 5). The increased concentrations of lactate after striatal malonate lesions confirm earlier reports, which reported similar values. Pretreatment with 50 mg/kg of 7-NI i.p. 0.5 h before the striatal lesion significantly attenuated this increase in striatal lactate concentrations (FIGS. 5 and 6). At 2 h after striatal injection of malonate in animals treated with 7-NI the lesion volume was significantly attenuated (34.9±27.7 mm$^3$, n=6) compared to vehicle treated controls (84.01±16.2 mm$^3$, n=5, p<0.01) as measured by $T_2$-weighted MR imaging.

Figure 7:
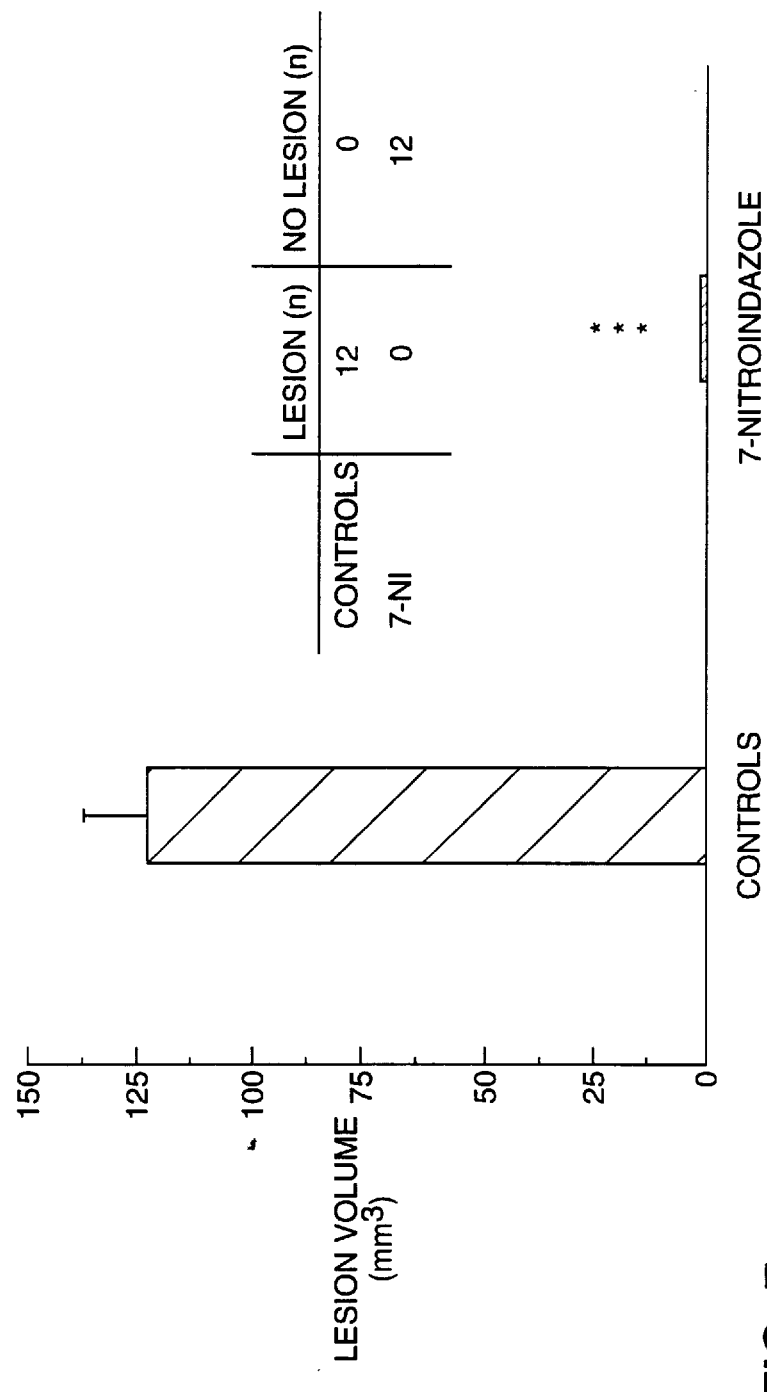
FIG. 7 shows the effects of 7-NI on striatal lesions produced by injection of 10 mg/kg of 3-NP every 12 h. In addition animals received either 25 mg/kg 7-NI or vehicle at the same time points. Animals were sacrificed at the 4th and 5th day. The table gives the number of animals showing a striatal lesion per group (n=12, $\omega^2$=0.0005). For calculation of lesion volume the lesions in both hemispheres were combined. ***=p<0.001 (Student's t-test).

Following subacute administration of 3-NP by intraperitoneal injection of 10 mg/kg every 12 h, rats developed severe dystonic posturing and rigidity by the fourth to fifth day. At these time points basal ganglia lesions were detectable by TTC staining. Vehicle and 7-NI treated animals were sacrificed in pairs. Treatment with 50 mg/kg of 7-NI every 12 h completely prevented striatal lesions produced by 3-NP (FIG. 7).

Figures 8A, 8B:
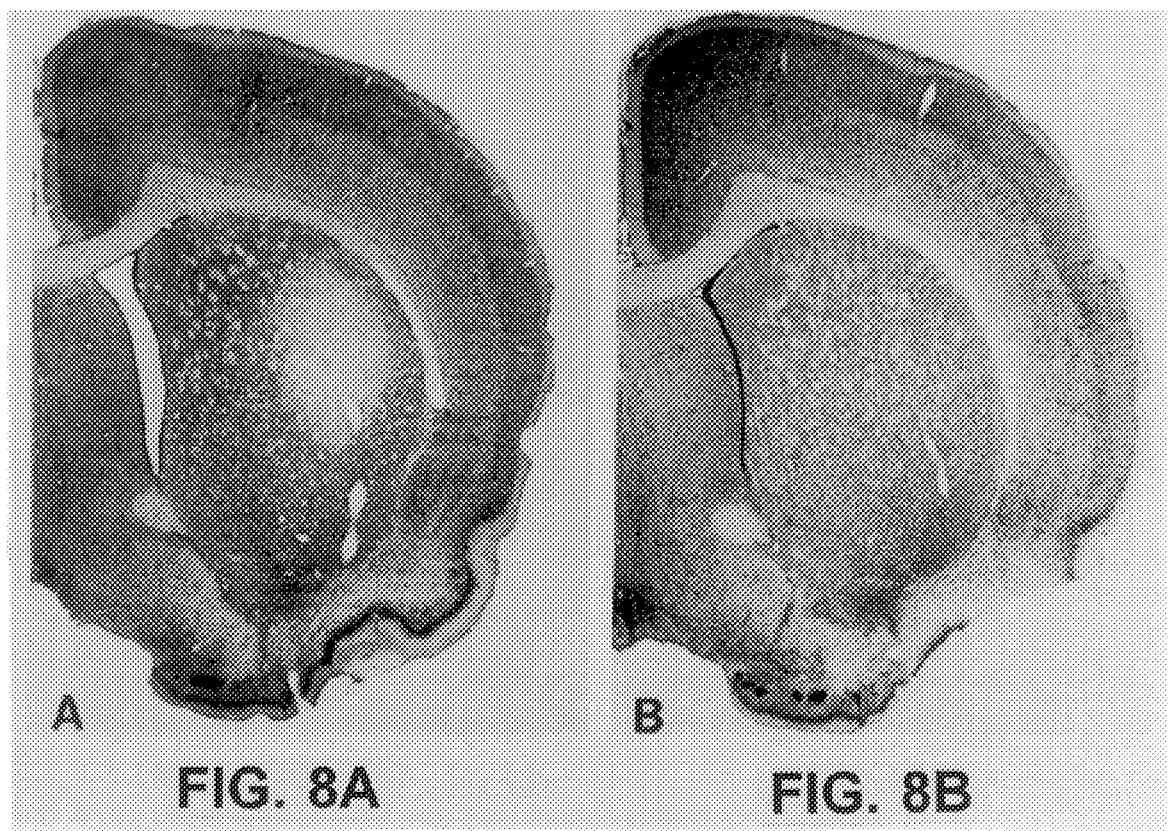
FIG. 8 shows the digitized photomicrographs of Nissl/NADPH-diaphorase stained sections through the caudate/putamen at the level of the anterior commissure of 3-nitropropionic acid (3-NP) treated rats. In A, a lesion (pale zone) is present in a rat treated with 3-NP alone. A higher magnification of the lesion is presented in C. There is marked neuronal loss and gliosis with NADP-diaphorase neuronal sparing (arrow heads). In contrast, the rat concomitantly treated with 3-NP and 7-nitroindazole (7-NI), the 7-NI provided complete protection (B and D).
Figures 8C, 8D:
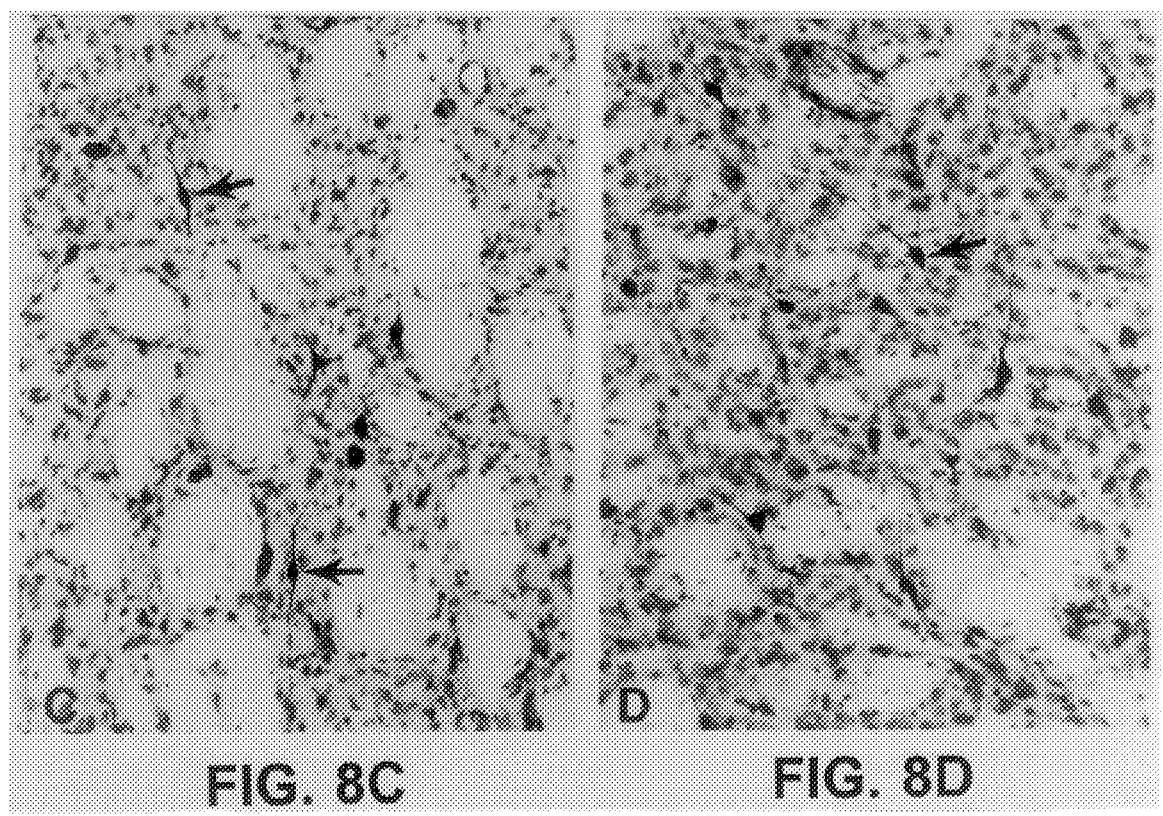
Figure 9:
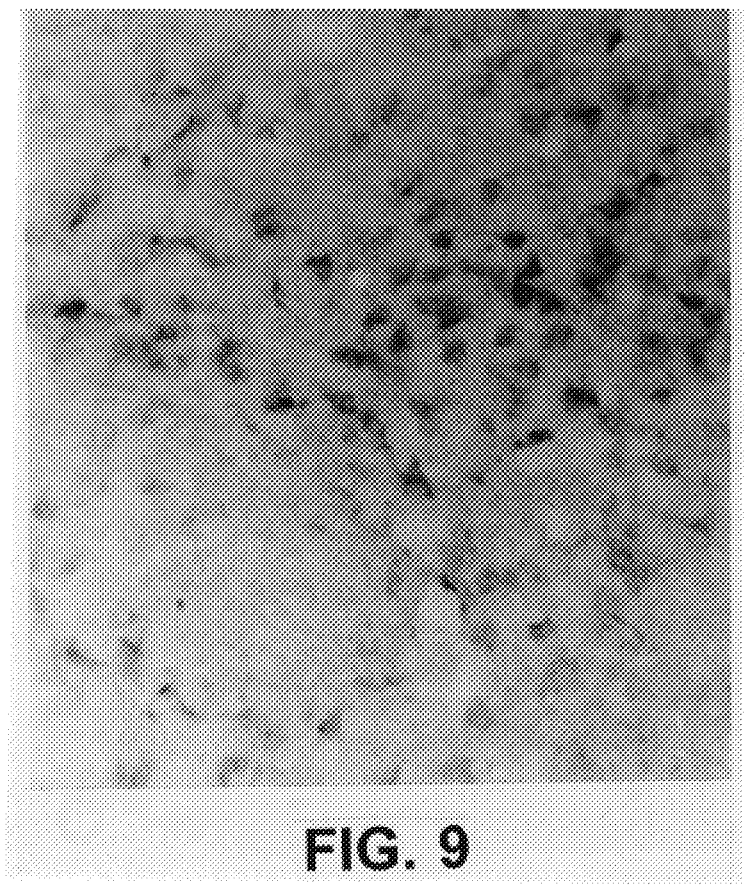
FIG. 9 shows the digitized photomicrograph of [8]hydroxydeoxyguanosine immunoreactivity around lesion site of FIG. 8A. Activity is present within neurons at this locus.

Subsequently we carried out a similar experiment with the aim to perform a histologic evaluation and immunocytochemistry for $^8$hydroxydeoxyguanosine and 3-nitrotyrosine. Again 10 mg/kg 3-NP was administered every 12 h. Vehicle and 7-NI treated animals were sacrificed in pairs (n=5). Knowing the results from the first experiment a second group of 7-NI treated animals was included. These animals were not sacrificed in pairs with the controls but only later when they developed rigidity and dystonic posturing. The controls were sacrificed after a median accumulative 3-NP dose of 80 mg/kg (range 70–90 mg/kg), whereas the 7-NI treated animals showed first symptoms after a median accumulative dose of 130 mg/kg (range 90–130 mg/kg, p<0.02, Mann-Whitney U test). The animals treated with 3-NP and vehicle showed extensive bilateral lesions in the striatum. Nissl stains showed loss of neurons with relative sparing of NADPH-diaphorase positive neurons (FIG. 8). In animals concomitantly treated with 3-NP and 7-NI, 7-NI completed protected the striatum from lesions. Compared to untreated controls and 7-NI treated 3-NP animals there was a marked increase of $^8$hydroxydeoxyguanosine immunoreactivity in vehicle treated 3-NP animals (FIG. 9).

Figure 10:
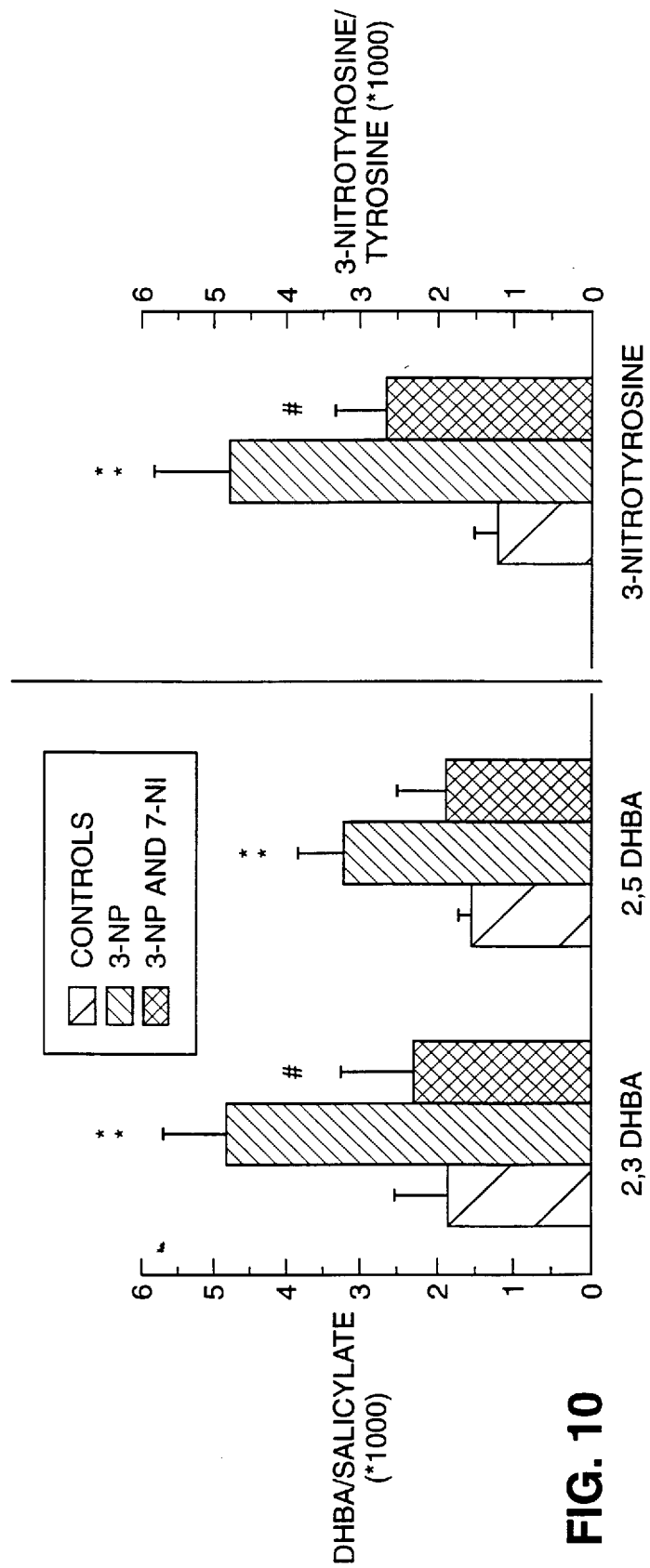
FIG. 10 shows the production of 2,3 and 2,5 DHBA and 3-nitrotyrosine by systemic treatment with 3-NP and effects of 7-NI (n=10). #=p<0.05 (ANOVA).

The concentrations of 2,3 and 2,5 DHBA, which are formed by salicylate reacting with ˙OH radicals, were significantly increased after 3-NP treatment compared to saline treated controls (FIG. 10). Treatment of 3-NP animals with 50 mg/kg of 7-NI significantly attenuated the increase of both metabolites. Peroxynitrite, a product of NO˙ reaction with $O_2$˙, has recently defined as a potent oxidant (Beckman et al. (1990) supra) and mediates the nitration of tyrosine (Beckman et al., 1992; Ischiropoulos et al., 1992). 3-NP treatment increased the ratio of 3-nitrotyrosine to tyrosine in the striatum compared to saline treated controls. Treatment with 50 mg/kg of 7-NI significantly attenuated the increase of 3-nitrotyrosine compared to vehicle treated animals in 3-NP animals (FIG. 9).

Figure 11A:
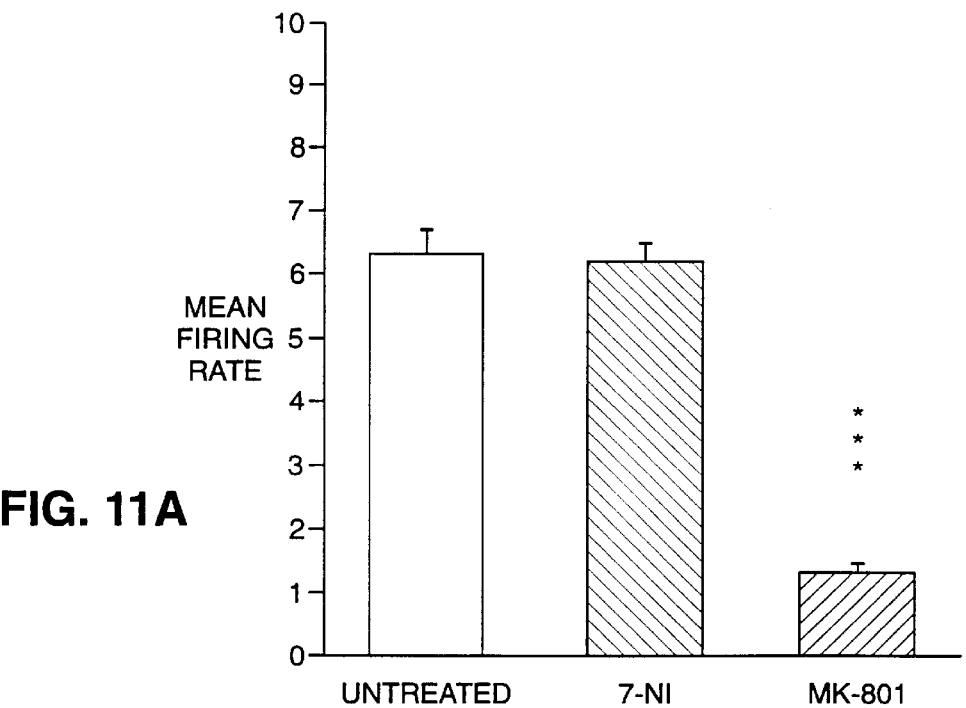
FIG. 11A shows the mean firing rate under three conditions, spontaneous, after injection of 7-NI (50 mg/kg i.p.) and after MK-801 (4mg/kg i.p.). Four animals received 7-NI and three of these also received MK-801. The spike counts were averaged. ***=p<0.001 (ANOVA).
Figure 11B:
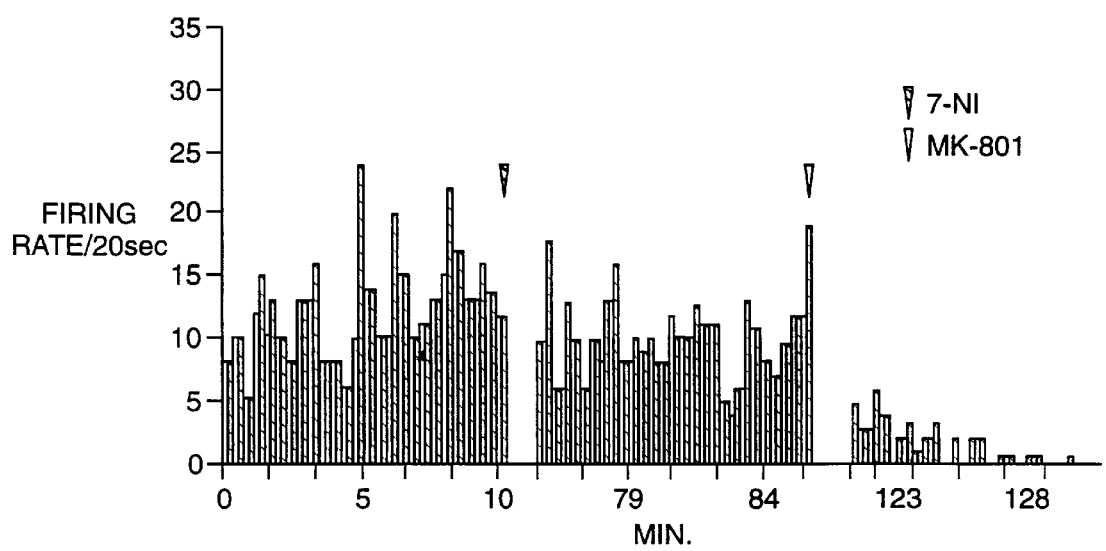
FIG. 11B shows the actual firing rate of neurons in the striatum from one of the test animals. The baseline spontaneous activity was recorded between 0 and 16 minutes. The first gap in the graph represents 60 min which elapsed from the time the animal was injected with 7-NI (black arrow head). During this gap no change in activity occurred. The second gap indicates the 30 minutes that passed after administering the MK-801 (white arrow).

The effects of 7-NI on spontaneous striatal electrophysiologic activity were compared with those of the NMDA antagonist MK-801 in urethane anesthetized rats. Spontaneous electrophysiologic activity of neurons returned within 30 minutes after insertion of an electrode into the striatum. After stabilization the mean spontaneous firing rate in the striatum was recorded (FIG. 10). Sixty minutes after i.p. treatment with 50 mg/kg of 7-NI the mean spontaneous firing rate was not significantly different from the baseline. To demonstrate that the NMDA channels were still functional after treatment with 7-NI, animals were then given the NMDA antagonist MK-801. The decrease in mean firing rate was rapid and profound (FIG. 11), suggesting that the effects of 7-NI were not mediated by an interaction with excitatory amino acid receptors.

Other Embodiments

Although 7-nitroindazole is a preferred compound for use in inhibiting a neuronal nitric oxide synthase, other nitroindazole compounds may be used as well, e.g. 3-bromo-7-nitroindazole. The invention also encompasses other compounds capable of inhibiting a neuronal nitric oxide synthase, e.g. 3-methyl-L-thiocitrulline.

Therapy

Patients diagnosed as suffering from a neurodegenerative disease are treated with a therapeutically effective amount of nitroindazole, e.g., 7-NI.

Nitroindazole may be formulated for parenteral administration, particularly in the form of liquid solutions or suspensions; for oral administration, particularly in the form of tablets or capsules; intranasally; topically; transdermally; or in a form suitable for use for implants.

Nitroindazole may be conveniently administered in a unit dosage form, and may be prepared by any of the techniques well known in the pharmaceutical art. Such techniques are described, for example, in *Remington's Pharmaceutical Sciences* ((1980) Mack Pub. Co., Easton, Pa.). Formulations for parenteral administration may contain common excipients such as sterile water or saline, polyalkylene glycols such as polyethylene glycol, oils of vegetable origin, hydrogenated napthalenes, and others of a similar nature. In particular, biocompatible, biodegradable lactide polymers, lactide/glycolide copolymers, or polyoxethylenepolyoxypropylene copolymers may be useful excipients to control the release of a compound of the invention. Other potentially useful parenteral delivery systems include ethylene-vinyl acetate copolymer particles, osmotic pumps, implantable infusion systems, and liposomes. Formulations for administration by inhalation may contain excipients such as, for example, lactose. Inhalation formulas may be aqueous solutions containing excipients such as, for example, polyoxyethylene 9-lauryl ether, glycocholate and deoxycholate, or they may be oily solutions for administration in the form of nasal drops, or as a gel to be applied intranasally. Compositions for parenteral administration may also include glycocholate for buccal administration, or cikic acid for vaginal administration.

The concentration of a nitroindazole formulation described herein in a physiologically acceptable mixture will vary depending on a number of factors including, for example, the dosage of the compound to be administered, the chemical characteristics of the compositions employed, and the route of administration. In general terms, the compositions of this invention may be provided in an aqueous physiological buffer solution containing about 0.01 to 10% w/v nitroindazole for parenteral administration. Typical dose ranges are from about 0.0001 mg nitroindazole/kg body weight to about 50 mg nitroindazole/kg of body weight per day. The preferred dosage of drug to be administered will depend on a number of variables including, for example, the severity of the neurodegenerative condition, the overall health status of the particular patient, the relative biological efficacy of the selected composition, the formulation of the excipients, and the route of administration. Further refinement of the calculations necessary to determine the appropriate dosage for treatment involving each of the above mentioned compositions is routinely made by those of ordinary skill in the art and is within the ambit of tasks routinely performed by them without undue experimentation, especially in light of the dosage information and assays disclosed herein. These dosages may be ascertained through use of the established assays for determining dosages utilized in conjunction with appropriate dose-response data.

Frequency of nitroindazole administration will vary, depending on factors such as the specific neurodegenerative disease being treated, the severity of the disease, and the general health of the patient. Nitroindazole may be administered as frequently as daily injections or as infrequently as once every 1–2 weeks. The dose regine may be repeated at intervals as needed to achieve the desired effect. Treatment will typically may be continued for the lifetime of a patient.

What is claimed is:

1. A method of treating a neurodegenerative disease in a human patient, the method comprising administering to said patient a therapeutically effective amount of a nitroindazole.

2. The method of claim 1, wherein said nitroindazole is 7-nitroindazole.

3. The method of claim 1, wherein said neurodegenerative disease is Parkinson's Disease.

4. The method of claim 1, wherein said neurodegenerative disease is Huntington's Disease.

5. The method of claim 1, wherein said neurodegenerative disease is Alzheimer's Disease.

6. The method of claim 1, wherein said neurodegenerative disease is amyotrophic lateral sclerosis.

7. The method of claim 1, wherein less than 50 mg/kg/dose of the nitroindazole is administered.

* * * * *